US012138026B2

(12) United States Patent
Grady et al.

(10) Patent No.: US 12,138,026 B2
(45) Date of Patent: Nov. 12, 2024

(54) SYSTEMS AND METHODS FOR PREDICTING PERFUSION DEFICITS FROM PHYSIOLOGICAL, ANATOMICAL, AND PATIENT CHARACTERISTICS (71) Applicant: HeartFlow Inc., Redwood City, CA (US)

(72) Inventors: Leo Grady, Millbrae, CA (US); Michiel Schaap, Redwood City, CA (US); Charles A. Taylor, Atherton, CA (US); Clara Jaquet, Paris (FR)

(73) Assignee: HeartFlow, Inc., Mountain View, CA (US)

( * ) Notice: Subject to any disclaimer, the term of this patent is extended or adjusted under 35 U.S.C. 154(b) by 1634 days.

(21) Appl. No.: 16/291,967

(22) Filed: Mar. 4, 2019

(65) Prior Publication Data

US 2019/0200881 A1 Jul. 4, 2019

Related U.S. Application Data

(63) Continuation of application No. 15/088,733, filed on Apr. 1, 2016, now Pat. No. 10,262,101.

(60) Provisional application No. 62/142,158, filed on Apr. 2, 2015.

(51) Int. Cl.
*A61B 5/026* (2006.01)
*A61B 5/02* (2006.01)
*G16H 30/20* (2018.01)
*G16H 50/20* (2018.01)
*G16H 50/50* (2018.01)

(52) U.S. Cl.
CPC .......... *A61B 5/026* (2013.01); *A61B 5/02007* (2013.01); *G16H 50/20* (2018.01); *G16H 50/50* (2018.01); *G16H 30/20* (2018.01)

(58) Field of Classification Search
None
See application file for complete search history.

(56) References Cited

U.S. PATENT DOCUMENTS

| | | |
|---|---|---|
| 9,349,178 B1 | 5/2016 | Itu et al. |
| 2003/0113827 A1 | 6/2003 | Burkoth |
| 2008/0132781 A1 | 6/2008 | Redel |
| 2011/0015520 A1 | 1/2011 | Meetz et al. |
| 2012/0053918 A1 | 3/2012 | Taylor |
| 2014/0073976 A1 | 3/2014 | Fonte et al. |
| 2015/0038860 A1 | 2/2015 | Fonte |
| 2015/0112182 A1 | 4/2015 | Sharma |
| 2015/0254418 A1 | 9/2015 | Sankaran |
| 2016/0287093 A1 | 10/2016 | Choi |
| 2016/0292382 A1 | 10/2016 | Grady |

FOREIGN PATENT DOCUMENTS

| | | |
|---|---|---|
| EP | 2 662 794 | 11/2013 |
| JP | H09176040 A | 7/1997 |
| JP | 2003509145 A | 3/2003 |
| JP | 2004500844 A | 1/2004 |
| JP | 2006320387 A | 11/2006 |
| JP | 2007068620 A | 3/2007 |
| JP | 2010516345 A | 5/2010 |
| JP | 2007529276 A | 7/2010 |
| JP | 2010524624 A | 7/2010 |
| JP | 2010213863 A | 9/2010 |
| JP | 2012071124 A | 4/2012 |
| JP | 2012531244 A | 12/2012 |
| JP | 2013515528 A | 5/2013 |
| JP | 2013233369 A | 11/2013 |
| JP | 2014032362 A | 2/2014 |
| JP | 2014196990 A | 10/2014 |
| JP | 2015039448 A | 3/2015 |
| KR | 1020100006248 A | 1/2010 |
| WO | 0010034 A1 | 2/2000 |
| WO | 0110301 A1 | 2/2001 |
| WO | WO 2015/153362 A1 | 10/2015 |
| WO | 2016161308 A1 | 11/2017 |

OTHER PUBLICATIONS

Tsoumpas, C. et al., "Fast generation of 4D PET-MR data from real dynamic MR acquisitions", Phys. Med. Biol, 2011, vol. 56, pp. 6597-6613.
Taylor, C., "Computational Fluid Dynamics Applied to Cardiac Computed Tomography for Noninvasive Quantification of Fractional Flow Reserve"; vol. 61, No. 22, Jun. 1, 2013; pp. 2233-2241.
Lucian Itu et al., "A Patient-specific Reduced-order Model for Coronary Circulation"; Biomedical Imaging, 2012 9th IEEE International Symposium on, IEEE, May 2, 2012; pp. 832-835.
Kim, H.J. et al.; "Patient-specific Modeling of Blood Flow and Pressure in Human Coronary Arteries"; Annals of Biomedical Engineering, Kluwer Academic Publishers—Plenum Publishers, NE, vol. 38, No. 10, Jun. 18, 2010; pp. 3195-3209.

(Continued)

*Primary Examiner* — Lori A. Clow (74) *Attorney, Agent, or Firm* — Bookoff McAndrews, PLLC (57) ABSTRACT

Systems and methods are disclosed for using patient specific anatomical models and physiological parameters to estimate perfusion of a target tissue to guide diagnosis or treatment of cardiovascular disease. One method includes receiving a patient-specific vessel model and a patent-specific tissue model of a patient anatomy; extracting one or more patient-specific physiological parameters (e.g. blood flow, anatomical characteristics, image characteristics, etc.) from the vessel or tissue models for one or more physiological states of the patient; estimating a characteristic of the perfusion of the patient-specific tissue model (e.g., via a trained machine learning algorithm) using the patient-specific physiological parameters; and outputting the estimated perfusion characteristic to a display.

20 Claims, 5 Drawing Sheets

(56) References Cited

OTHER PUBLICATIONS

International Search Report dated Jun. 28, 2016, in related PCT/US2016/025595 (13 pages).
EP Examination Report, issued in related Application No. 2,981,464 dated Feb. 22, 2019 (3 pages).
Mouridsen, Kim, et al. "Bayesian estimation of cerebral perfusion using a physiological model of microvasculature." Neuroimage 33.2 (2006): 570-579.
Fung G S K et al, "Realistic simulation of regional myocardial perfusion defects for cardiac SPECT studies", Nuclear Science Symposium Conference Record (NSS/MIC), 2010 IEEE, IEEE, (Oct. 30, 2010), doi:10.1109/NSSMIC.2010.5874362, ISBN 978-1-4244-9106-3, pp. 3061-3064, XP032054637.

SYSTEMS AND METHODS FOR PREDICTING PERFUSION DEFICITS FROM PHYSIOLOGICAL, ANATOMICAL, AND PATIENT CHARACTERISTICS

RELATED APPLICATIONS

This application is a continuation of and claims the benefit of priority to U.S. patent application Ser. No. 15/088,733 filed Apr. 1, 2016, which claims priority under 35 U.S.C. § 119(e) to U.S. Provisional Application No. 62/142,158, filed Apr. 2, 2015, all of which are hereby incorporated herein by reference in their entireties.

FIELD OF THE DISCLOSURE

Various embodiments of the present disclosure relate generally to disease assessment, treatment planning, and related methods. More specifically, particular embodiments of the present disclosure relate to systems and methods for estimating perfusion of a target tissue.

BACKGROUND

Coronary artery disease is a common ailment that affects millions of people. Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack. Significant strides have been made in the treatment of coronary artery disease including both medical therapy (e.g. statins) or surgical alternatives (e.g., percutaneous coronary intervention (PCI) and coronary artery bypass graft surgery (CABG)). Invasive assessments are commonly used to assess the type of treatment a patient may receive. However, indirect or noninvasive assessments for formulating a patient treatment are being explored and developed.

Heart disease is typically viewed as resulting from vessel disease, in particular, narrowing of the vessels or blockage inside vessel lumens in a way that impacts blood flow. One way to measure the extent of this narrowing or blockage is through a perfusion scan, since perfusion is the flow of blood through a vascular network (e.g., arteries, capillaries, etc). Currently, perfusion scans may be costly and may expose the patient to unnecessary radiation. Thus, a desire exists to use available patient information to estimate perfusion in certain target tissue, where the estimated perfusion data may be used to simulate a familiar scan type, for example, single positron emission computed tomography (SPECT) or positron emission tomography (PET), so that a physician may be familiar with how to read the image. Furthermore, a desire exists to improve treatment of cardiovascular disease by better assessing the severity of cardiovascular disease.

The foregoing general description and the following detailed description are exemplary and explanatory only and are not restrictive of the disclosure.

SUMMARY

According to certain aspects of the present disclosure, systems and methods are disclosed for using available information to estimate perfusion of a target tissue to guide diagnosis or treatment of cardiovascular disease.

One method includes: receiving a patient-specific vessel model and a patent-specific tissue model of a patient's anatomy; extracting one or more patient-specific physiological parameters of the patient from the vessel or tissue models at one or more physiological states of the patient; estimating a characteristic of the perfusion of blood through the patient-specific tissue model using the patient-specific physiological parameters; and outputting the estimated characteristic of the perfusion of blood to a display.

In accordance with another embodiment, system for estimating patient-specific perfusion, the system comprising: a data storage device storing instructions for determining patient-specific characteristics of the perfusion of blood; and a processor configured to execute the instructions to perform a method including the steps of: receiving a patient-specific vessel model and a patent-specific tissue model of a patient's anatomy; extracting one or more patient-specific physiological parameters of the patient from the vessel or tissue models at one or more physiological states of the patient; estimating a characteristic of the perfusion of blood through the patient-specific tissue model using the patient-specific physiological parameters; and outputting the estimated characteristic of the perfusion of blood to a display.

In accordance with another embodiment, a non-transitory computer readable medium for use on a computer system containing computer-executable programming instructions for estimating patient-specific characteristics of the perfusion of blood, the method comprising: receiving a patient-specific vessel model and a patent-specific tissue model of a patient's anatomy; extracting one or more patient-specific physiological parameters of the patient from the vessel or tissue models at one or more physiological states of the patient; estimating a characteristic of the perfusion of blood through the patient-specific tissue model using the patient-specific physiological parameters; and outputting the estimated characteristic of the perfusion of blood to a display.

Additional objects and advantages of the disclosed embodiments will be set forth in part in the description that follows, and in part will be apparent from the description, or may be learned by practice of the disclosed embodiments. The objects and advantages on the disclosed embodiments will be realized and attained by means of the elements and combinations particularly pointed out in the appended claims.

It is to be understood that both the foregoing general description and the following detailed description are exemplary and explanatory only and are not restrictive of the detailed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

FIG. 4 may also disclose a method of performing steps 208 or 322 in FIG. 2 and FIG. 3, respectively, for determining an estimate of tissue perfusion.

FIG. 5 is a block diagram of the method disclosed in FIG. 4 in greater detail. Furthermore, FIG. 5 also discloses an exemplary method for estimating patient-specific perfusion characteristics from vessel geometry and patient-specific physiological parameters (e.g., anatomical information, secondary information, and blood supply information), using machine learning, according to an exemplary embodiment of the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Coronary artery disease is a common ailment, by which blood flow to the heart may be restricted. While significant strides have been made in the treatment of coronary artery disease, the treatment is often misplaced or excessive. For example, patients often undergo invasive surgical treatments, or perfusion scans which may be costly and/or expose the patient to unnecessary radiation. Patients are sometimes subjected to treatments that may not change their condition. In some situations, patients even undergo treatments that ultimately worsen their condition. Thus, a need exists to accurately assess the severity of cardiovascular disease and/or predict perfusion to aid in selecting a course of treatment.

Cardiovascular disease may be linked to vessel disease, meaning vessel narrowing or blockage. A cardiac perfusion scan may measure the amount of blood in the heart muscle at different physiological states. A "physiological state" may refer to a resting patient state, a hyperemic state, an exercise state, a postprandial state, a gravitational state, an emotional state, a state of hypertension, a medicated state or a combination thereof. A perfusion scan is often performed to determine what may be causing chest pain and to determine if the tissue of the heart is supplied with an adequate flow of blood, or to determine how much heart muscle has been damaged from the heart attack.

During the scan, images of the heart are generated after a radioactive tracer is intravenously administered to the patient. The radioactive tracer travels through the blood and into the heart muscle. As the tracer moves through the heart muscle, tissues that have sufficient blood flow absorb the tracer. Tissue that does not absorb the tracer may not receive enough blood or may have been damaged by a heart attack. Two sets of images may be generated during a cardiac perfusion scan. The at rest images are then compared with the stress or non-rest images and a level of perfusion in the target tissue may be determined. A "target tissue" may refer to a tissue and/or organ in which the blood supply and/or perfusion characteristics may be estimated.

Therefore, an understanding of perfusion in the target tissue may be clinically important. An understanding of perfusion may improve an evaluation of the severity of disease and of the appropriateness of treatment. The present disclosure may benefit patients and doctors by either estimating perfusion under conditions in which perfusion may be difficult to measure, and/or by employing measurements of cardiac perfusion to more accurately assess the severity of vessel disease in different physiological conditions. The perfusion images generated may simulate images generated from a familiar scan type such as PET and/or SPECT. The simulated images may provide ease of reading and understanding to physicians who are trained to read PET and/or SPECT images. For the purposes of the disclosure: "patient" may refer to any individual or person for whom diagnosis or treatment analysis is being performed, or any individual or person associated with the diagnosis or treatment analysis of one or more individuals.

Figure 1:
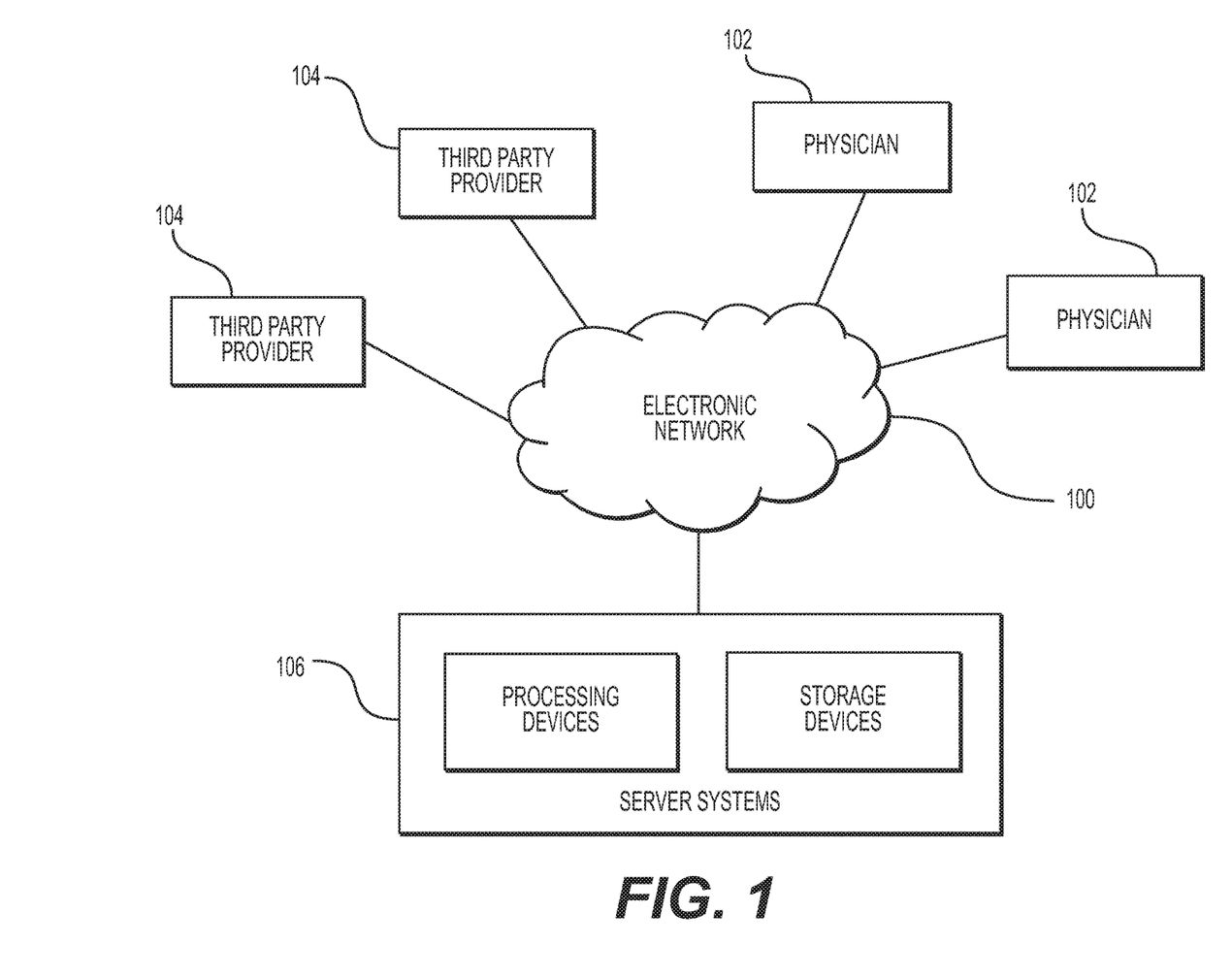
FIG. 1 is a block diagram of an exemplary system and network for predicting perfusion to guide diagnosis or treatment of cardiovascular disease, according to an exemplary embodiment of the present disclosure.
Figure 2:
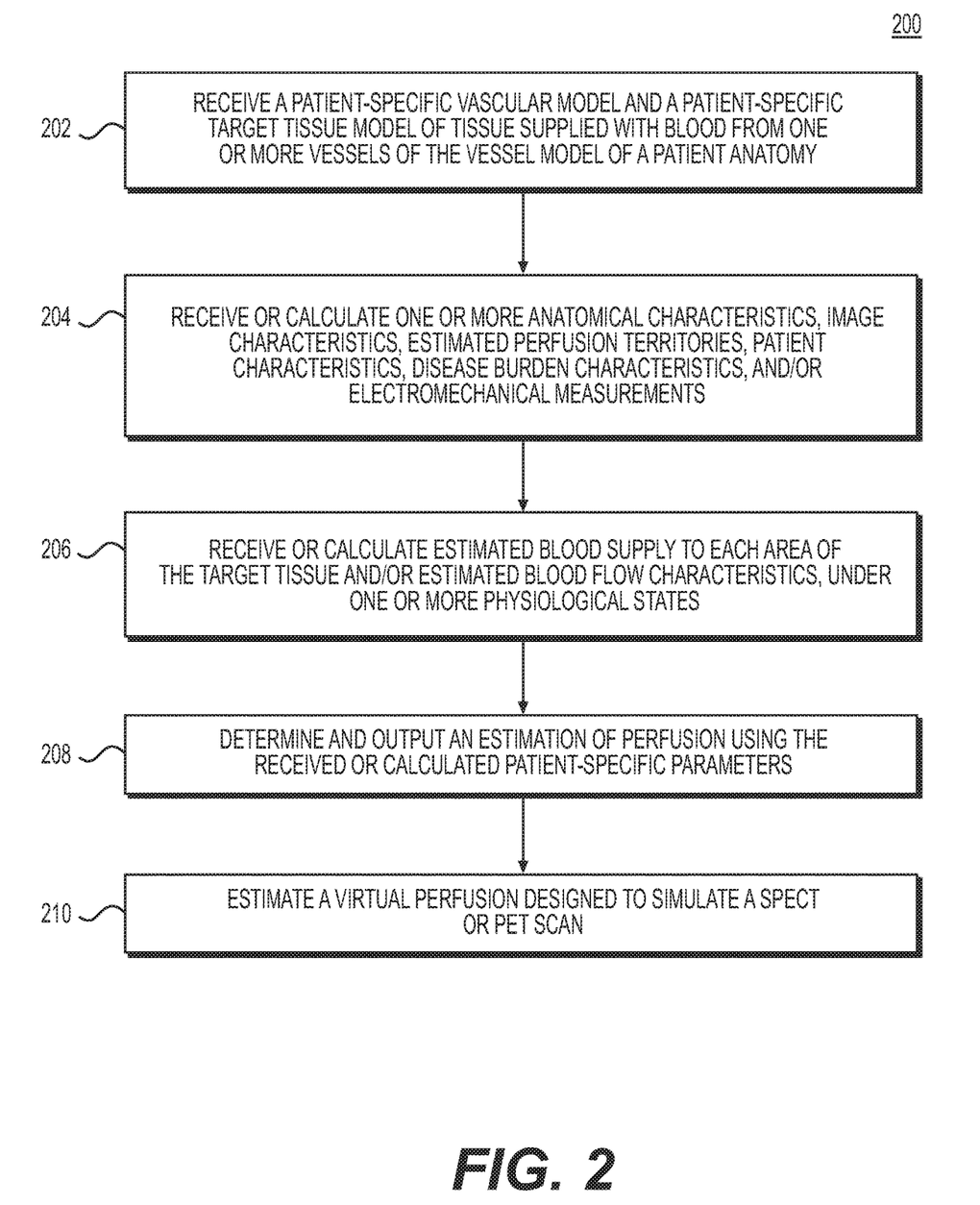
FIG. 2 is a block diagram of an general method of estimating perfusion, according to a general embodiment of the present disclosure.
Figure 3:
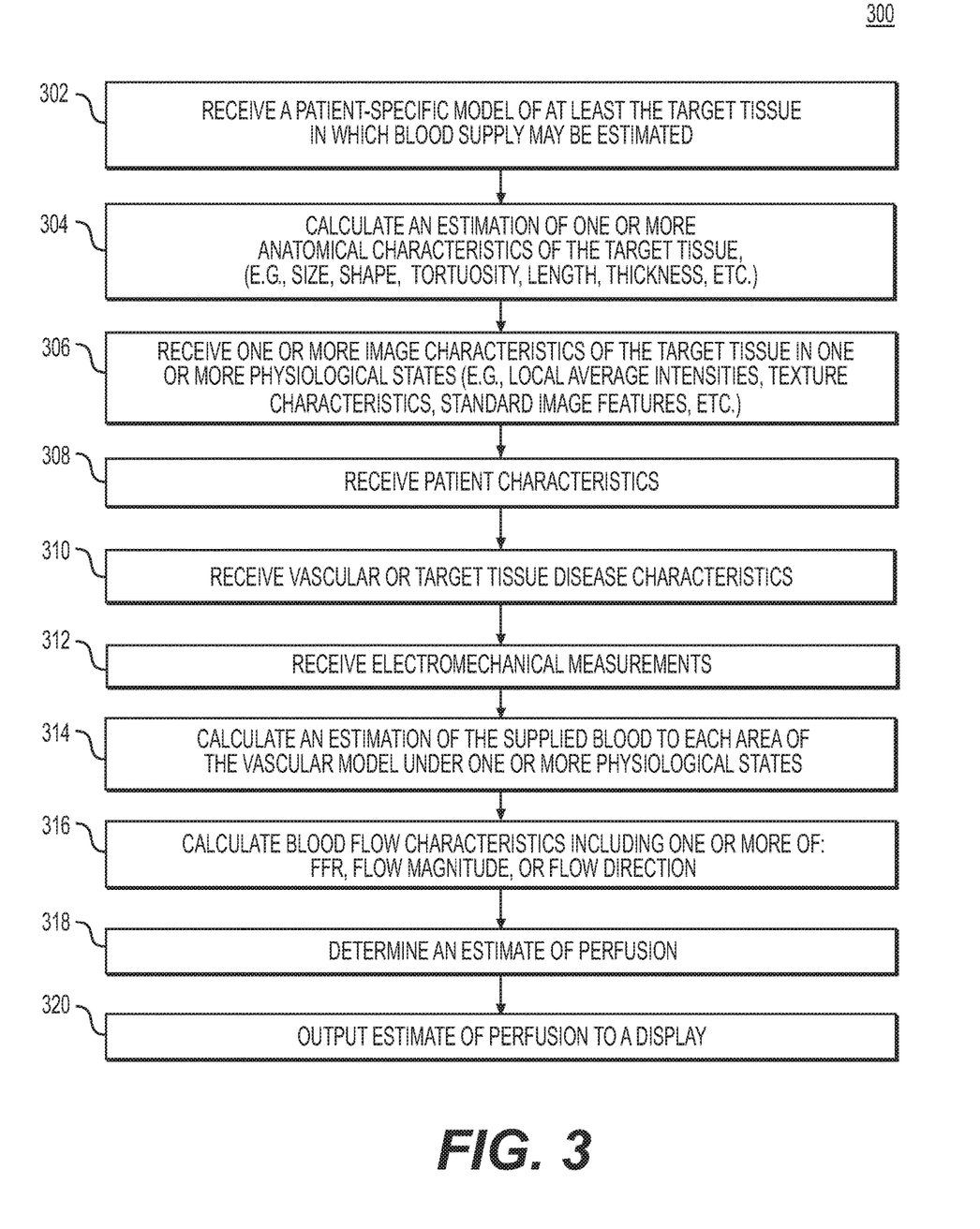
FIG. 3 is a block diagram of an exemplary method of estimating perfusion, according to an exemplary embodiment of the present disclosure.
Figure 4:
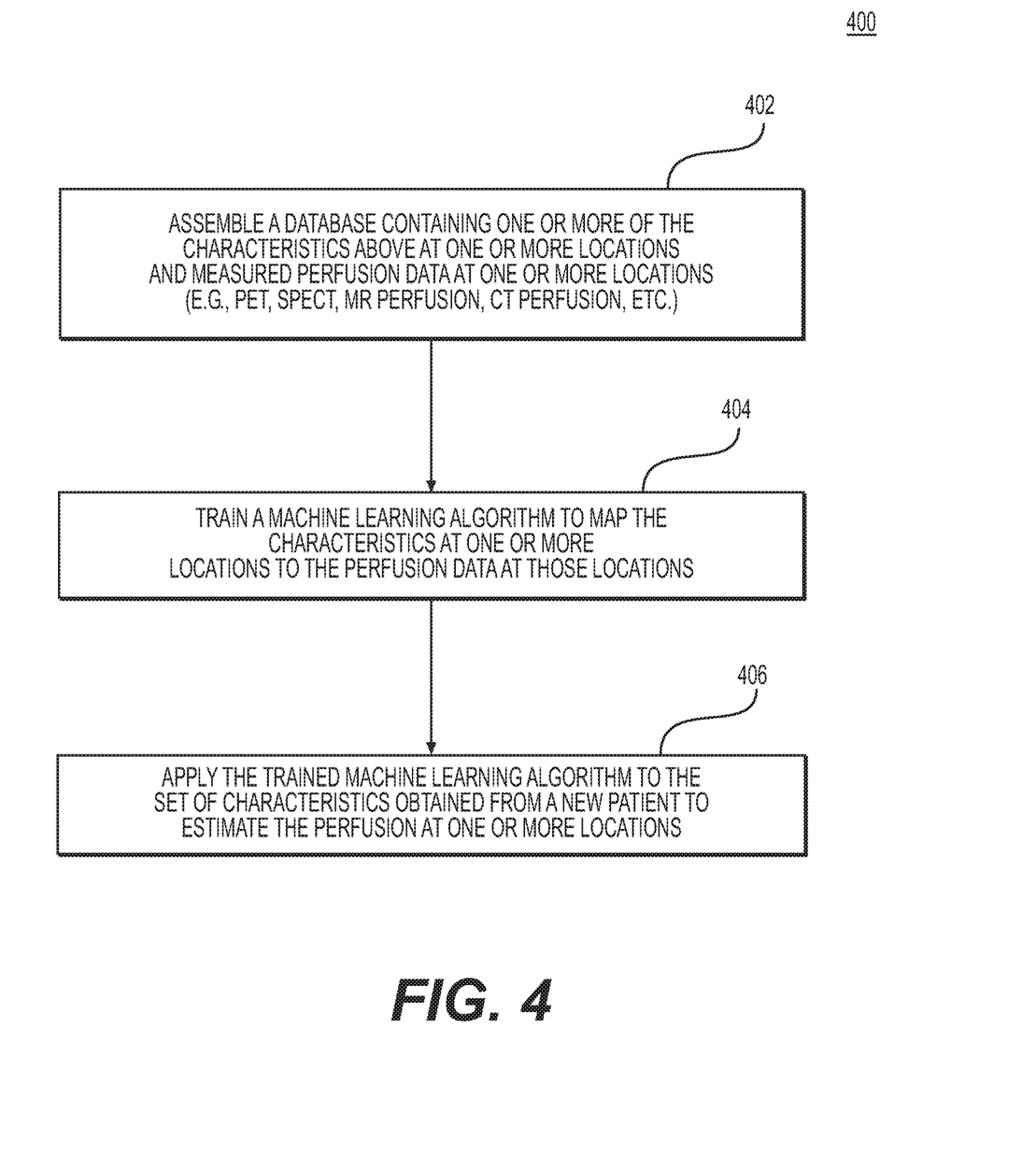
FIG. 4 is a block diagram of an exemplary method of estimating perfusion, using machine learning, according to an exemplary embodiment of the present disclosure.
Figure 5:
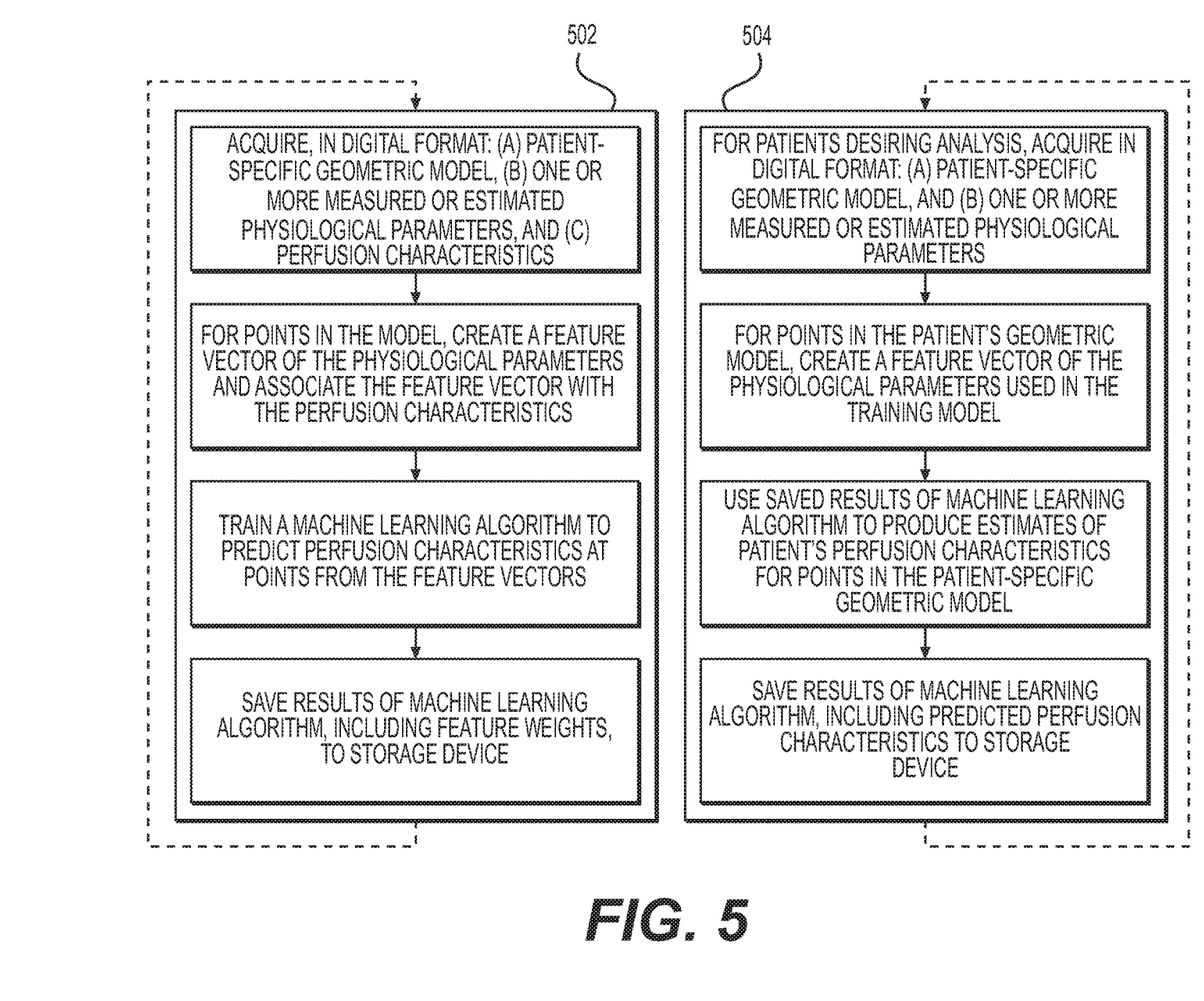

While FIG. 1 provides an abstract view of the system and network of the current disclosure, FIG. 2 illustrates a general embodiment of a method for estimating one or more characteristics of the perfusion of blood, and FIG. 3 lays out a more specific embodiment. Furthermore, both FIG. 2, and FIG. 3 disclose the step of determining an estimate of the perfusion of blood through a tissue. FIG. 4 illustrates an exemplary method for performing the step of determining an estimate of one or more characteristics of the perfusion of blood through a tissue using a trained machine learning algorithm. FIG. 5 examines the method disclosed in FIG. 4 in further detail.

Referring now to the figures in more detail, FIG. 1 depicts a block diagram of an exemplary system 100 and network for estimating cardiac perfusion to guide diagnosis or treatment of cardiovascular disease, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity, or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

FIG. 2 depicts a general embodiment of an exemplary method 200 for estimating cardiac perfusion to guide diagnosis or treatment of cardiovascular disease. The method of FIG. 2 may be performed by server systems 106, based on information, images, and data received from physicians 102 and/or third party providers 104 over electronic network 101.

In one embodiment, step 202 may include receiving a patient-specific vessel model of a patient's anatomy and a patient-specific target tissue model stored in an electronic storage medium of the storage system 106. An "electronic storage medium" may include, but is not limited to, a hard drive, network drive, cloud drive, mobile phone, tablet, or the like that may or may not be affixed to a display screen. Specifically, receiving the patient-specific vessel model and the patient-specific target tissue model may include either generating the patient-specific vessel model and/or the patient-specific target tissue model at the server system 106, or receiving the patient-specific vessel model and/or the patient-specific target tissue model over an electronic network (e.g., electronic network 101). The patient-specific vessel model and the patient-specific target tissue model may include a cardiovascular model of a specific person. In one embodiment, the vessel model and the target tissue model may be derived from images of the person acquired via one or more available imaging or scanning modalities (e.g., computed tomography (CT) scans and/or magnetic resonance imaging (MR)). For example, step 202 may include receiving CT and/or MR images of a person's heart. Step 202 may further include generating, from the received images, a patient-specific cardiovascular model for the particular person. The electronic storage medium may include, but is not limited to, a hard drive, network drive, cloud drive, mobile phone, table, or the like.

In one embodiment, steps 204 and 206 may include receiving or calculating one or more patient-specific physiological parameters. These patient-specific physiological parameters may be received or calculated from the received vessel model and/or target tissue model. These patient-specific physiological parameters may include anatomical characteristics, image characteristics, as well as secondary characteristics related to the patient and/or the patient's anatomy (e.g., patient characteristics, disease burden characteristics, and electromechanical measurements). The patient-specific physiological parameters may also include parameters related to blood circulation, including an estimation of the blood supply to each area of a target tissue and/or blood flow characteristics, under one or more physiological states.

Specifically, step 204 may include receiving or calculating one or more anatomical characteristics, image characteristics, patient characteristics, disease burden characteristics, and/or electromechanical characteristics, under one or more physiological states. One instance of a physiological state may be a resting state. Another physiological state may be a physiological state other than the resting state, or an "active" physiological state. Active physiological states may include hyperemia, various levels of exercise, post prandial, positional (e.g., supine-upright), gravitational (e.g. G-forces, zero gravity, etc.), or a combination thereof. In one embodiment, the patient-specific physiological parameters may be obtained from sources other than the vessel model and/or target tissue model.

In one embodiment, step 206 may include receiving or calculating an estimated supplied blood to each area of a target tissue or to each vessel in a vascular network and/or estimated blood flow characteristics, under one or more physiological states. These estimations may be based on a measurement (e.g., by measuring through imaging) or via an estimation of supplied blood in a resting state (e.g., based on a 3D simulation, a 1D simulation, or a learned relationship).

In one embodiment, step 208 may include determining and outputting an estimation of perfusion in the vessel of the vessel model or area in the target tissue model, using joint prior information. The joint prior information may refer to the one or more received patient-specific physiological parameters (e.g., received or calculated medical image characteristics, anatomical characteristics, blood supply to the target tissue, blood flow characteristics, patient characteristics, disease burden characteristics, electromechanical measurements, etc.) determined in steps 204 and 206. In one embodiment, determining an estimation of perfusion may involve determining an estimation of supplied blood at one or more vessel locations of the person's vessel model, while the person is in a given physiological state. This determination may also be based on a measurement of blood flow (e.g., by imaging) or via an estimation of blood flow in a resting state (e.g., based on a 3D simulation, a 1D simulation, or a learned relationship). In one embodiment, step 208 may include calculating an estimation of the perfusion territories of the target tissue related to the vascular model. This estimation may be determined, by using a nearest-neighbor (e.g., Voronoi diagram) approach to assign locations in the target tissue to the closest supplying vessel in the vascular model. The estimation may also be determined using a microvascular estimation technique from an anatomical model, for example, by using a constrained constructive optimization approach. In one embodiment, step 208 may be performed by a processor. The processor may estimate perfusion at one or more locations of the target tissue in the vascular model in one or more psychological states by machine learning. In one embodiment, step 208 may further include outputting the estimation of perfusion to an electronic storage medium (e.g., hard disk, network drive, portable disk, smart phone, tablet etc.) and/or to a display screen. In one embodiment, the output perfusion estimates may be displayed in greyscale or color in 2D or 3D. The calculated perfusion estimates may be overlaid on the anatomical model of the target tissue and/or overlaid on an image of the target tissue.

In one embodiment, step 210 may include estimating virtual perfusion designed to simulate a SPECT or a PET scan in one or more physiological states. In one embodiment, the estimation may be performed by modeling contrast agent in the concentrations given by the perfusion estimates. In another embodiment, the said estimation may involve performing a Monte Carlo simulation to estimate the collimation of photons or positrons at virtual collimator locations. Using the collimator estimation, a SPECT or PET image may be reconstructed using standard tomographic techniques. The estimated virtual perfusion image may be saved to an electronic storage medium and/or displayed on a monitor.

FIG. 3 depicts an exemplary embodiment of method 300 for estimating cardiac perfusion to guide diagnosis or treatment of cardiovascular disease. The method of FIG. 3 may be performed by server systems 106, based on information, images, and data received from physicians 102 and/or third party providers 104 over electronic network 101.

In one embodiment, step 302 may include receiving a patient-specific vascular model of at least the target tissue of a patient anatomy in an electronic storage medium of the storage system 106. Specifically, receiving the patient-specific anatomic model may include either generating the patient-specific anatomical model at the server system 106, or receiving one over an electronic network (e.g., electronic network 101). The patient-specific anatomic model may include a cardiovascular model of a specific person. In one embodiment, the anatomic model may be derived from images of the person acquired via one or more available imaging or scanning modalities (e.g., CT scans and/or magnetic resonance imaging). For example, step 302 may include receiving CT and/or MRI images of a person's heart. Step 302 may further include generating, from the received images, a patient-specific cardiovascular model for the particular person. The electronic storage medium may include, but is not limited to, a hard drive, network drive, cloud drive, mobile phone, tablet, or the like.

In one embodiment, step 304 may include calculating an estimation of one or more of the anatomical characteristics of the target tissue. The anatomical characteristics may include, but are not limited to, vessel size, vessel shape, tortuosity, thickness, and/or estimated perfusion territories within a target tissue or vascular network. This calculation may be based on a measurement (e.g., by measuring the anatomical characteristics from imaging) or via an estimation of the anatomical characteristics in a resting state (e.g., based on a 3D simulation, a 1D simulation, or a learned relationship).

In one embodiment, step 306 may include receiving one or more image characteristics of the target tissue. The image characteristics may be obtained from CT scan images, MRI images, ultrasound images, PET images, or SPECT images. The images may capture the vascular model in one or more physiological states (e.g., rest, stress, active). The image characteristics of the target tissue or vessels may be received or calculated in one or more locations of the vascular model. The image characteristics may include, but are not limited to, local average intensities at one or more image resolutions, differences of the average intensities (e.g., calculated via wavelet bases, using for example, Haar wavelets), texture characteristics (e.g., Haralick texture features), and any standard image features including histograms, gradients, SIFT, or steerable filters etc.

In one embodiment, step 308 may include receiving patient characteristics. The patient characteristics may include, but are not limited to, age, gender, smoking history, height, weight, diabetic status, hypertensive status, ethnicity, family history, blood type, prior history of drug use, and/or genetic history. The patient characteristics may be obtained via the electronic network 100 or from the patient's physician 102 or from a third party provider 103.

In one embodiment, step 310 may include receiving the vascular or target tissue disease characteristics. The target tissue disease characteristics may include, but are not limited to, the presence and extent of plaque buildup within the arteries, the presence of plaque characteristics (e.g., spotty calcification, low attenuation plaque, napkin-ring sign, positive remodeling), patient level or vessel level calcium scores, tissue viability information, vessel wall motion, vessel wall thickness, and/or ejection fraction information.

In one embodiment, step 312 may include receiving electromechanical measurements. The electromechanical measurements may include, but are not limited to, electrocardiography (ECG) measurements, or invasive electrophysiology (EP) measurements.

In one embodiment, step 314 may include calculating an estimation of the supplied blood to each area of the target tissue under one or more physiological states. One instance of a first physiological state may be a resting state. This calculation may be based on a measurement (e.g., by measuring through imaging) or via an estimation of supplied blood in a resting state (e.g., based on a three-dimensional (3D) simulation, a one-dimensional (1D) simulation, or a learned relationship). Another physiological state may be a physiological state other than the resting state, or an "active" physiological state. One instance of such a physiological state may include hyperemia. Other non-resting physiological states may include, various levels of exercise, post prandial, positional (e.g., supine-upright), gravitational (e.g. G-forces, zero gravity, etc.).

In one embodiment, step 316 may include calculating one or more blood flow characteristics of the target tissue. In one embodiment, the blood flow characteristics may include, but is not limited to, a fractional flow reserve value (FFR), flow direction, and/or flow magnitude and is determined by an estimation of blood flow to the target tissue. In one embodiment, the blood flow characteristic may be calculated by several means, including, but not limited to, invasive measurements (e.g., invasive FFR, thrombosis in myocardial infarction (TIMI), or microspheres), calculation using a blood flow simulation model (e.g., a 3D or 1D fluid simulation model, calculation, or TAFE), calculation using imaging characteristics (e.g., TAG or CCO), or calculation using a machine learning estimation of blood supply based on anatomical or imaging features. In one embodiment, step 316 may include calculating an estimation of the blood flow in the perfusion territories of the target tissue related to the vascular model. This estimation may be determined by using a nearest-neighbor (e.g., Voronoi diagram) approach to assigning locations in the target tissue to the closest supplying blood vessel in the vascular model. The estimation may also be determined using a microvascular estimation technique from an anatomical model, for example, by using a constrained constructive optimization approach. In one embodiment, step 316 may be performed by a processor. The processor may estimate perfusion at one or more locations of the target tissue in the vascular model in one or more psychological states by machine learning.

In one embodiment, step 318 may include calculating, using a processor, an estimate of the perfusion at one or more locations in the target tissue related to the vascular model. The estimation of perfusion may be calculated for one or more physiological states using the one or more of the patient specific patient-specific physiological parameters (e.g., image characteristics, anatomical characteristics, estimated blood supply, estimated blood flow characteristics, estimated perfusion territories, patient characteristics, disease burden characteristics, and/or electromechanical measurements). In one embodiment, this calculation may be performed by training a machine learning algorithm using a database of patients with known perfusion characteristics and known patient-specific physiological parameters, including, but not limited to, the image characteristics, anatomical characteristics, estimated perfusion territories, disease burden characteristics, and/or electromechanical measurements. In one embodiment step 318 may be performed using a processor.

In one embodiment, step 320 may include outputting the estimation of perfusion to an electronic storage medium (e.g., hard disk, network drive, portable disk, smart phone, tablet etc.) and/or to a display screen. In one embodiment, the output perfusion estimates may be displayed in greyscale or color in 2D or 3D. In one embodiment, the output perfusion estimates may be overlaid or superimposed on the anatomical model of the target tissue and/or overlaid or superimposed on an image of the target tissue. In one embodiment, this determination may be performed by training a machine learning algorithm using a database of patients with known perfusion characteristics and known patient-specific physiological parameters. In one embodiment, the perfusion estimates may be used to estimate a virtual perfusion image designed to simulate a SPECT or PET image in one or more of the physiological states of the patient. In one embodiment, the virtual perfusion image may be saved into an electronic storage medium and/or output to a display. The estimation of the virtual perfusion image may be performed by modeling a contrast image in the concentrations given by the perfusion estimates, performing a Monte Carlo simulation to estimate the collimation of photons or positrons at a plurality of virtual collimator locations, and/or using the collimator estimation to reconstruct a SPECT or PET image using standard tomographic techniques. The estimated virtual perfusion image may be similar in readability and design to a SPECT or PET scan image, and thus the physician may be familiar with how to analyze the estimated perfusion image.

The above recited steps of methods 200 and 300 may be used to estimate perfusion in a variety of tissues, including, but not limited to, the myocardium using a coronary vascular model, the brain using a cerebral vascular model, muscle tissue using a peripheral vascular model, the liver using a hepatic vascular model, the kidney using a renal vascular model, the bowel using a visceral vascular model, and in other organs including the spleen and pancreas, using a vascular model for vessels supplying blood to the target organ.

In one embodiment, the perfusion estimation may also be used to enhance a blood flow simulation by using more accurate boundary conditions to perform a simulation or estimation of blood flow characteristics.

In one embodiment, treatment planning and diagnosis may be improved by virtually changing the input information (e.g. the vascular model, tissue model, patient-specific physiological parameters, etc.) and predicting the effects on perfusion in the target tissue based on the changed inputs.

FIG. 4 depicts an exemplary embodiment of method 400 for training a machine learning algorithm to determine an estimate of perfusion at one or more locations in the target tissue in one or more physiological states. The method of FIG. 4 may be performed by server systems 106, based on information, images, and data received from physicians 102 and/or third party providers 104 over electronic network 101.

In one embodiment, step 402 may include assembling a database containing one or more of the patient-specific physiological parameters at one or more locations in the vascular and/or target tissue model and the estimated or measured perfusion data those locations. The "patient-specific physiological parameters" may refer to one or more of the received or calculated medical image characteristics, anatomical characteristics, perfusion territories, blood supply to the target tissue, blood flow characteristics, patient characteristics, disease burden characteristics, and/or electromechanical measurements. The locations may be from the patient-specific vascular and/or target tissue models, or images obtained from one or more available imaging or scanning modalities, including, but not limited to, PET, SPECT, MR perfusion, and/or CT perfusion.

In one embodiment, step 404 may include training a machine learning algorithm to map the one or more patient-specific physiological parameters at one or more locations of the vascular and/or target tissue model to the perfusion data at those locations. The machine learning algorithm may take many forms, including, but not limited to, a multi-layer perceptron, deep learning, support vector machines, random forests, k-nearest neighbors, Bayes networks, etc.

In one embodiment, step 406 may include applying the trained machine learning algorithm to the set of patient-specific physiological parameters of the vascular model and/or target tissue obtained from a new patient to estimate the perfusion data at one or more locations.

FIG. 5 is a block diagram of an exemplary method for estimating patient-specific blood flow characteristics from vessel geometry and physiological information, according to an exemplary embodiment of the present disclosure. The method of FIG. 5 may be performed by server systems 106, based on information received from physicians 102 and/or third party providers 104 over electronic network 100.

In one embodiment, the method of FIG. 5 may include a training method 502, for training one or more machine learning algorithms based on patient-specific physiological parameters from numerous patients and measured or estimated perfusion characteristics, and a production method 504 for using the machine learning algorithm results to predict a particular patient's perfusion characteristics.

In one embodiment, training method 502 may involve acquiring, for each of a plurality of individuals, e.g., in digital format: (a) a patient-specific geometric model, (b) one or more measured or estimated patient-specific physiological parameters, and (c) values of perfusion characteristics. Training method 502 may then involve, for one or more points in each patient's model, creating a feature vector of the patients' physiological parameters and associating the feature vector with the values of perfusion characteristics. Training method 1002 may then train a machine learning algorithm (e.g., using processing devices of server systems 106) to predict perfusion at each point of a geometric model, based on the feature vectors and estimated perfusion characteristics. Training method 502 may then save the results of the machine learning algorithm, including feature weights, in a storage device of server systems 106. The stored feature weights may define the extent to which patient-specific physiological parameters and/or anatomical geometry are predictive of certain perfusion characteristics.

In another embodiment, training method 502 may be performed based on FFR estimates generated using computational fluid dynamics (CFD) techniques for a plurality of patients. Training method 502 may then involve associating an estimated FFR value with every point in a patient's geometric model, and then creating a feature vector of the patient-specific physiological parameters and associating the feature vector with FFR estimates. Training method 502 may then train a machine learning algorithm (e.g., using processing devices of server systems 106) to predict perfusion at each point of a geometric model, based on the feature vectors and estimated FFR.

In one embodiment, the production method 504 may involve estimating perfusion characteristics for a particular patient, based on results of executing training method 502. In one embodiment, production method 504 may include acquiring, e.g. in digital format: (a) a patient-specific geometric model, and (b) one or more measured or estimated patient-specific physiological parameters. For multiple points in the patient's geometric model, production method 504 may involve creating a feature vector of the patient-specific physiological parameters used in the training mode. Production method 504 may then use saved results of the machine learning algorithm to produce estimates of the patient's perfusion characteristics for each point in the patient-specific geometric model. Finally, production method 504 may include saving the results of the machine learning algorithm, including predicted perfusion characteristics, to a storage device of server systems 106.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for estimating perfusion of blood in tissues of patients, the method comprising:

receiving a patient-specific vessel model of one or more vessels of a patient and a patient-specific tissue model of a target tissue supplied by the one or more vessels, wherein the target tissue has a plurality of areas, wherein each of the patient-specific vessel model and the patient-specific tissue model is derived from medical images of the patient;

determining one or more patient-specific values of one or more anatomical or physiological parameters based on the patient-specific vessel model or the patient-specific tissue model;

determining an estimated supplied blood to each area of the plurality of areas of the target tissue;

computing an estimate of a perfusion of blood in the target tissue based on the determined patient-specific values of the one or more anatomical or physiological parameters and the determined estimated supplied blood to each area of the plurality of areas of the target tissue;

generating a virtual scan including a visualization of the computed estimate of the perfusion of blood, wherein the visualization of the computed estimate of the perfusion of blood is overlaid on an image of the target tissue to simulate a SPECT scan or a PET scan; and displaying the virtual scan on an electronic display.

2. The computer-implemented method of claim 1, wherein the one or more anatomical or physiological parameters include a characteristic of blood flow to a plurality of regions of the one or more vessels or the target tissue under one or more physiological states.

3. The computer-implemented method of claim 2, wherein the characteristic of perfusion of blood flow includes a fractional flow reserve, flow magnitude, flow direction, or a combination thereof.

4. The computer-implemented method of claim 1, wherein the one or more anatomical or physiological parameters include vessel size, vessel shape, vessel tortuosity, vessel length, vessel thickness, estimated territories of the perfusion of blood within a tissue or vascular network, or a combination thereof.

5. The computer-implemented method of claim 1, wherein the one or more patient-specific values includes a value for a resting patient state, a hyperemic state, an exercise state, a postprandial state, a gravitational state, an emotional state, a state of hypertension, a medicated state, or a combination thereof.

6. The computer-implemented method of claim 1, further comprising receiving a characteristic of a medical image of the target tissue or the one or more vessels, the characteristic of the medical image including local average intensities, texture characteristics, standard image, or a combination thereof.

7. The computer-implemented method of claim 1, further comprising receiving patient characteristics, disease characteristics of the target tissue, electromechanical characteristics, or a combination thereof.

8. The computer-implemented method of claim 1, wherein the patient-specific vessel model and the target tissue respectively include:
a coronary vascular model and a myocardium;
a cerebral vascular model and a brain;
a peripheral vascular model and a muscle;
a hepatic vascular model and a liver;
a renal vascular model and a kidney; or
a visceral vascular model and a bowel.

9. The computer-implemented method of claim 1, further comprising:
adjusting the one or more patient-specific values of the one or more anatomical or physiological parameters to represent an effect of a treatment; and
computing a new estimate of perfusion of blood in the patient-specific tissue model using the adjusted one or more patient-specific values.

10. The computer-implemented method of claim 1, wherein the simulating the SPECT scan or the PET scan includes modeling a concentration of a contrast agent using the computed estimate of the perfusion of blood.

11. The computer-implemented method of claim 1, wherein the simulating the SPECT scan or the PET scan includes estimating a collimation of photons or positrons at virtual collimator locations.

12. A system for estimating perfusion of blood in tissues of patients, the system comprising:
a data storage device storing instructions for determining patient-specific characteristics of the perfusion of blood; and
a processor configured to execute the instructions to perform operations including:
receiving a patient-specific vessel model of one or more vessels of a patient and a patient-specific tissue model of a target tissue supplied by the one or more vessels, wherein the target tissue has a plurality of areas, wherein each of the patient-specific vessel model and the patient-specific tissue model is derived from medical images of the patient;
determining one or more patient-specific values of one or more anatomical or physiological parameters based on the patient-specific vessel model or the patient-specific tissue model;
determining an estimated supplied blood to each area of the plurality of areas of the target tissue;
computing an estimate of a perfusion of blood in the target tissue based on the determined patient-specific values of the one or more anatomical or physiological parameters and the determined estimated supplied blood to each area of the plurality of areas of the target tissue;
generating a virtual scan including a visualization of the computed estimate of the perfusion of blood, wherein the visualization of the computed estimate of the perfusion of blood is overlaid on an image of the target tissue to simulate a SPECT scan or a PET scan; and
displaying the virtual scan on an electronic display.

13. The system of claim 12, wherein the one or more anatomical or physiological parameters include an estimated or measured blood flow to a plurality of regions of the one or more vessels or tissue, anatomical characteristics, or a combination thereof.

14. The system of claim 12, the operations further comprising receiving patient characteristics, disease characteristics of the target tissue, electromechanical characteristics, or a combination thereof.

15. The system of claim 12, wherein the patient-specific vessel model and the target tissue respectively include:
a coronary vascular model and a myocardium;
a cerebral vascular model and a brain;
a peripheral vascular model and muscle;
a hepatic vascular model and a liver;
a renal vascular model and a kidney; or
a visceral vascular model and a bowel.

16. The system of claim 12, wherein the simulating the SPECT scan or the PET scan includes modeling a concentration of a contrast agent using the computed estimate of the perfusion of blood.

17. The system of claim 12, wherein the simulating the SPECT scan or the PET scan includes estimating a collimation of photons or positrons at virtual collimator locations.

18. A non-transitory computer-readable medium for use on a computer system containing computer-executable programming instructions that, when executed by a processor of the computer system, cause the computer system to perform operations including:

receiving a patient-specific vessel model of one or more vessels of a patient and a patient-specific tissue model of a target tissue supplied by the one or more vessels, wherein the target tissue has a plurality of areas, wherein each of the patient-specific vessel model and the patient-specific tissue model is derived from medical images of the patient;

determining one or more patient-specific values of one or more anatomical or physiological parameters based on the patient-specific vessel model or the patient-specific tissue model;

determining an estimated supplied blood to each area of the plurality of areas of the target tissue;

computing an estimate of a perfusion of blood in the target tissue based on the determined patient-specific values of the one or more anatomical or physiological parameters and the determined estimated supplied blood to each area of the plurality of areas of the target tissue;

generating a virtual scan including a visualization of the computed estimate of the perfusion of blood, wherein the visualization of the computed estimate of the perfusion of blood is overlaid on an image of the target tissue to simulate a SPECT scan or a PET scan; and displaying the virtual scan on an electronic display.

19. The non-transitory computer-readable medium of claim 18, wherein the simulating the SPECT scan or the PET scan includes modeling a concentration of a contrast agent using the computed estimate of the perfusion of blood.

20. The non-transitory computer-readable medium of claim 18, wherein the simulating the SPECT scan or the PET scan includes estimating a collimation of photons or positrons at virtual collimator locations.

* * * * *